United States Patent
Gasbarro et al.

(10) Patent No.: US 7,499,713 B2
(45) Date of Patent: Mar. 3, 2009

(54) SYSTEMS AND METHODS FOR CONDITION AND LOCATION MONITORING OF MOBILE ENTITIES

(75) Inventors: Henry Frank Gasbarro, Marina del Ray, CA (US); Brian Bieber, Redondo Beach, CA (US); Jay Frederking, Irivne, CA (US); Joseph Edwin Carpenter, Long Beach, CA (US)

(73) Assignee: Northrop Grumann Corporation, Los Angeles, CA (US)

( * ) Notice: Subject to any disclaimer, the term of this patent is extended or adjusted under 35 U.S.C. 154(b) by 634 days.

(21) Appl. No.: 11/116,836

(22) Filed: Apr. 28, 2005

(65) Prior Publication Data
US 2006/0246922 A1    Nov. 2, 2006

(51) Int. Cl.
*H04Q 7/20* (2006.01)
(52) U.S. Cl. .............. 455/456.1; 455/404.2; 455/456.6; 455/414.1
(58) Field of Classification Search ... 455/456.1–456.6, 455/457, 67.7, 404.1–404.2, 67.11, 100, 455/556.1, 414.1–414.2; 340/572.1, 573.4, 340/539, 852.49
See application file for complete search history.

(56) References Cited

U.S. PATENT DOCUMENTS

| | | | |
|---|---|---|---|
| 4,487,583 A | 12/1984 | Brucker et al. | |
| 4,948,371 A | 8/1990 | Hall | |
| 5,199,874 A | 4/1993 | Campagnuolo et al. | |
| 5,292,254 A | 3/1994 | Miller et al. | |
| 5,771,001 A * | 6/1998 | Cobb | 340/573.1 |
| 6,065,404 A | 5/2000 | Ripingill, Jr. et al. | |
| 6,072,396 A * | 6/2000 | Gaukel | 340/573.4 |
| 6,489,604 B1 | 12/2002 | Fardin et al. | |
| 6,530,841 B2 | 3/2003 | Bull et al. | |
| 6,561,809 B1 | 5/2003 | Lynch et al. | |
| 6,569,011 B1 | 5/2003 | Lynch et al. | |
| 6,755,653 B2 | 6/2004 | Varshneya | |
| 6,799,971 B2 | 10/2004 | Healy et al. | |
| 6,821,124 B2 | 11/2004 | Healy et al. | |

(Continued)

FOREIGN PATENT DOCUMENTS

EP    0846440 A1    6/1998

(Continued)

OTHER PUBLICATIONS

Sear Report for corresponding GB 0607747.3, claims searched: 1-27; search completed Aug. 15, 2006.

*Primary Examiner*—John J Lee
(74) *Attorney, Agent, or Firm*—Tarolli, Sundheim, Covell & Tummino LLP

(57) ABSTRACT

Systems and methods are disclosed for condition and location monitoring of mobile entities. One embodiment of a system may comprise a sensor system that measures at least one real time parameter associated with the mobile entity and compares the measured at least one real time parameter to at least one predetermined threshold to determine at least one condition of the mobile entity. The system may also comprise a situational awareness (SA) beacon having a global position satellite (GPS) device that determines a location of the mobile entity and a transceiver, wherein the SA beacon periodically transmits location information and condition information via the transceiver to a central control for display.

23 Claims, 7 Drawing Sheets

U.S. PATENT DOCUMENTS

| | | |
|---|---|---|
| 2001/0029011 A1 | 10/2001 | Dagani et al. |
| 2002/0111201 A1 | 8/2002 | Lang |
| 2003/0027103 A1 | 2/2003 | Preston et al. |
| 2003/0137419 A1* | 7/2003 | Gehlot et al. ............ 340/572.1 |
| 2004/0033472 A1* | 2/2004 | Varshneya .................. 434/23 |
| 2004/0121292 A1 | 6/2004 | Chung et al. |

FOREIGN PATENT DOCUMENTS

| | | |
|---|---|---|
| GB | 2399204 A | 2/2005 |
| WO | WO 99/31575 | 6/1999 |

* cited by examiner

SYSTEMS AND METHODS FOR CONDITION AND LOCATION MONITORING OF MOBILE ENTITIES

TECHNICAL FIELD

This invention relates to the situational awareness, and more particularly to systems and methods for condition and location monitoring of mobile entities.

BACKGROUND OF THE INVENTION

In situational awareness systems, it is desirable to maintain consistent periodic communication with one or more mobile entities. Such consistent communications are useful in situations have a risk of incapacitation of the mobile entity, such as battlefield applications, recreational activities in rugged environments, or civilian search and rescue operations. If the periodic communications from the mobile entities cease, a search can be carried out at the last reported location. A variation on this theme could include an automated communications unit that periodically broadcasts a signal to other communication units, such that the signal itself can be employed to locate the mobile entity. However, most situational awareness systems only determine the presence of a user's most recent reported location. Therefore, an estimate of the location of the user needs to be made based on other known previously reported information. Additionally, the real-time condition of the mobile entity is unknown and assumptions need to be made based on other known previously reported information.

SUMMARY OF THE INVENTION

Figure 1:
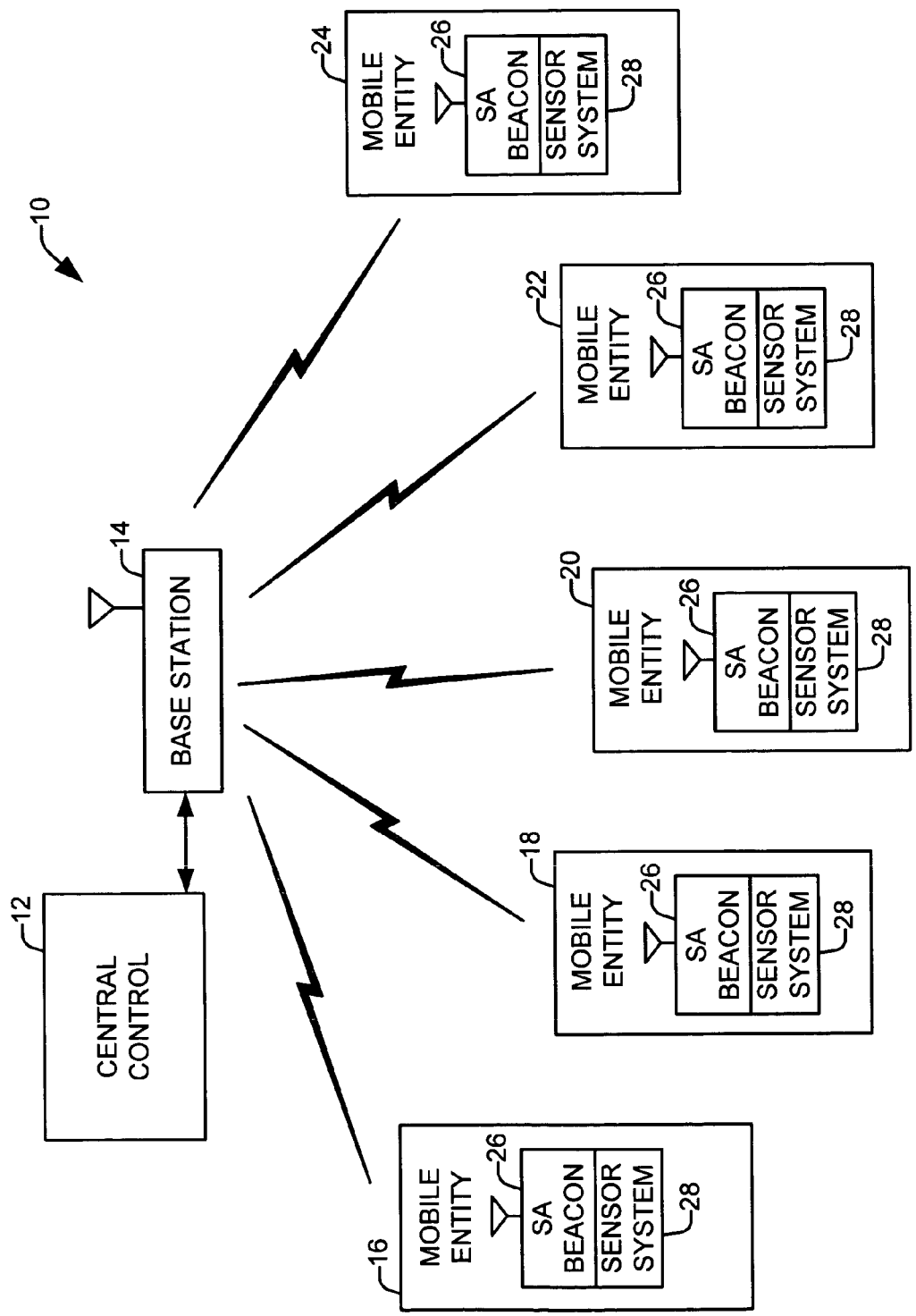
FIG. 1 illustrates a block diagram of a situational awareness system in accordance with an aspect of the present invention.

In accordance with an aspect of the invention, a system is provided for condition and location monitoring of a mobile entity. The system may include a sensor system that measures at least one real time parameter associated with the mobile entity and compares the measured at least one real time parameter to at least one predetermined threshold to determine at least one condition of the mobile entity. The system further comprises a situational awareness (SA) beacon comprising a global position satellite (GPS) device that determines a location of the mobile entity and a transceiver, wherein the SA beacon periodically transmits location information and condition information via the transceiver to a central control for display.

In accordance with yet another aspect of the present invention, a situational awareness system is provided. The situational awareness system comprises a plurality of condition and location monitoring systems that determine at least one condition and a location of an associated mobile entity, wherein the at least one condition is based on a measured real time parameter value associated with an associated mobile entity being compared to at least one predetermined threshold. The situational awareness system further comprises a central control that receives the condition information and location information from the plurality of condition and location monitoring systems and displays icons representing a plurality of mobile entities in a geographic map representing an area in which the plurality of mobile entities move. The condition information associated with each of the plurality of mobile entities is displayed in a geographic map by varying an icon color associated with an icon representing a respective mobile entity, and the location information associated with each of the plurality of mobile entities is displayed by locating the icon in a location of the geographic map.

In accordance with yet another aspect of the present invention, a method is provided for condition and location monitoring of a mobile entity. The method comprises comparing at least one measured real time parameter associated with a mobile entity to at least one predetermined threshold to determine at least one condition associated with the mobile entity, determining a location of the mobile entity and transmitting condition information and location information associated with the mobile entity to a central control.

DETAILED DESCRIPTION OF THE INVENTION

The present invention relates to systems and methods for condition and locations monitoring of mobile entities in a situational awareness system. The systems and methods employ a sensor system to measure one or more real time parameters associated with a mobile entity. The one or more real time parameters are compared to one or more predetermined thresholds to determine one or more conditions associated with the mobile entity. The one or more conditions are provided to a situational awareness (SA) beacon. The SA beacon includes a global positioning satellite (GPS) device for determining a location of the mobile entity. The SA beacon can provide location and condition information to a central controller. The SA beacon can also provide parameter information to the central controller. The central controller or the SA beacon can determine if one or more of the conditions has changed such that an event has occurred. The central controller provides a situational awareness display that displays the location and condition of the mobile entity, for example, in a geographic map. The display can also provide parameter information associated with the condition of the mobile entity. This can be repeated for a plurality of mobile entities.

FIG. 1 illustrates a situational awareness system 10 in accordance with an aspect of the present invention. The system 10 includes a plurality of mobile entities 16, 18, 20, 22 and 24. The mobile entities 16, 18, 20, 22 and 24 can be, for example, people, vehicles, devices carried by people, satellites or other mobile entities. Each mobile entity includes a sensor system 28 that measures one or more real time parameters associated with a respective mobile entity. For example, the one or more real time parameters can include parameters associated with a living mobile entity, such as body temperature, heart rate, heart rhythm, breathing rhythm, blood pressure, position, or posture. The one or real time parameters can include parameters associated with a non-living entity, such as a number of times a weapon discharges, a power level of a power source, current levels of an electronic system, resource usage of a communication system, fuel levels of a vehicle, temperature levels of an electronic device or vehicle and other real time parameters associated with a non-living mobile entity. The one or real time parameters can include environmental parameters such as environmental temperature, humidity, wind speed or precipitation.

The one or more real time parameters can be compared to one or more predetermined thresholds to determine a condition of the mobile entity. The one or more predetermined thresholds can reside in a table to establish different threshold ranges in which a parameter falling with in a given threshold range can establish a condition of the mobile entity. The one or more predetermines thresholds can also include time, such that if a parameter resides at a certain threshold range for a certain time period, a given condition has been met. For example, if a heart patient who is being monitored has an increase in heart rate or an irregular heart beat for a certain time period it can be an indication of a likelihood of an upcoming heart attack. Also, if a patient's posture or position appears to be face down or slumped over, and other parameters indicate unconsciousness, such as breathing rate or heart rate for a certain period of time, an alert condition may be met, such that the patient is experiencing a heart attack or stroke. Time can also be employed for non-living entities. For example, if a power supply voltage is below a certain level for a short period it can be as a result of a temporary increase in load. However, if the power supply voltage is below a certain level for a longer period it can be as a result of a low battery condition.

Each mobile entity 16, 18, 20, 22 and 24 includes a situational awareness (SA) beacon 26 that stores and updates the one or more conditions associated with the respective mobile entity provided by the sensor system 28. The SA beacon 26 also includes a GPS device for determining a location (e.g., longitude and latitude) of the mobile entity. The SA beacon 26 includes a transceiver coupled to one or more antennas for wirelessly communicating to and from a central control 12. The system 10 can also include a base station 14 for routing communications between each SA beacon 26 and the central control 12. The base station 14 can be terrestrial based and/or satellite based, such that the transceiver and the one or more antennas can transmit over land based radio frequencies or satellite based frequencies. The transceiver can transmit communications based on one of a number of different wireless protocols (e.g., IEEE 802.11b, 802.16, 801.20), a frequency hopping spread spectrum, based on different modulation schemes, encryption schemes and/or over a satellite frequency band, such as an L-Band. The base station 14 can be a satellite, a cellular base station, or a transceiver coupled via a cable to the central control 12.

Each SA beacon 26 can periodically provide condition information, location information and optionally parameter information associated with the condition information to the central control 12. Alternatively, the central control 12 can periodically poll (e.g., via a status request) each SA beacon 26 for condition information and location information, and optionally parameter information. Furthermore, condition information and location information can be provided to the central control 12 only when a change in condition has occurred or a condition change that results in an event. For example, a person's status has changed to injured, dead, critical or some other status that would be alarming to a user at the central control 12. Additionally, a fuel level, power level, or ammunition level of a non-living human entity has become alarmingly low.

The central control 12 provides a situational awareness display that displays the location and condition of each of the mobile entities 16, 18, 20, 22 and 24. The condition of each mobile entity can be provided textually or by different colors of an icon representing the mobile entity. For example, a person that is in a normal condition can be displayed in white, an injured person in grey, a dead person in black and a person that is in a critical condition and needing immediate attention in red. The display can also provide parameter information associated with the condition of the mobile entity. For example, a central control user can click on an icon, for example, using a computer mouse pointer displaying parameters associated with a condition of the mobile entity. Alternatively, the parameters can be displayed with the icon or can be part of a generated report that can be displayed or printed. The location information of the mobile entity can be displayed as longitude and latitude data, or the icon can be displayed in a geographic map associated with an area in which the mobile entity moves. The central control 12 can be operative to transmit reset requests, status requests, and transmit software updates to the SA beacon devices 26 and/or sensor systems 28.

Figure 2:
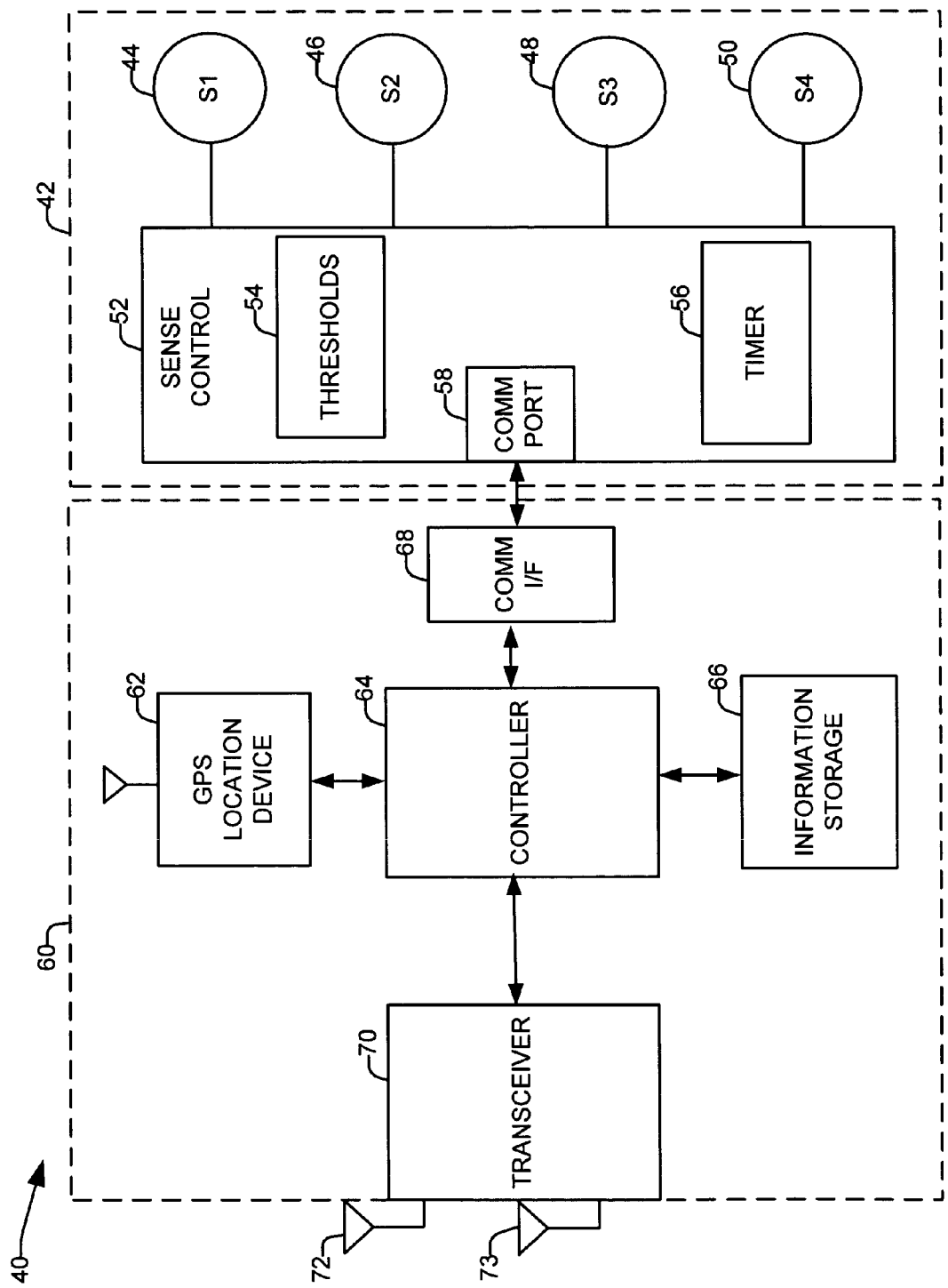
FIG. 2 illustrates a block diagram of a condition and location monitoring system for a mobile entity in accordance with an aspect of the present invention.

FIG. 2 illustrates a condition and location monitoring system 40 for a mobile entity in accordance with an aspect of the present invention. The system 40 includes a sensor system portion 42 and a SA beacon portion 60. The sensor system 42 and SA beacon portion 60 can be fabricated as an integrated unit or coupled together as separate units. The sensor system 42 includes one or more sensors (S1-S4) 44, 46, 48 and 50 coupled to a sensor control 52. Although the example illustrates four sensors, the sensor system can employ N sensors, where N is an integer greater than zero. The one or more sensors 44, 46, 48 and 50 measure one or more real time parameters associated with a mobile entity. The one or more sensors 44, 46, 48 and 50 provide electrical signals to the sensor control 52 indicative of a measured parameter. The sensor control 52 contains one or more thresholds 54 that can be compared to one or more real time parameters to determine one or more conditions associated with the mobile entity. The sensor control 52 also includes a timer or clock 56 for determining an amount of time that a parameter resides between a given threshold range to determine if a given condition has occurred. The timer or clock 56 can also be employed to provide time information in which a condition change has occurred. The sensor control 52 also includes a communication port 58 for transmitting condition, parameter and time information to the SA beacon portion 60.

The SA beacon portion 60 includes a GPS location device 62 for determining location information associated with the mobile entity. The GPS location device 62 includes a GPS antenna and periodically performs a GPS routine to determine longitude and latitude of the mobile entity. A controller 64 receives or retrieves the location information and stores the information in an information storage 66 (e.g., random access memory). The controller 64 communicates with the sensor control 52 through a communication interface 68 communicatively coupled to the communication port 58. The communication interface 68 can be an infrared interface, a RF interface or a wire interface to the communication port 58. The controller 64 receives or retrieves the condition, parameter and time information from the sensor control 52 and stores the information in the information storage 66.

The SA beacon portion 60 includes a transceiver 70 coupled to a first antenna 72 and an optional second antenna 73. For example, the first antenna 72 can be a terrestrial based antenna and the second antenna 73 can be a satellite based antenna to provide concurrent terrestrial and satellite communications. The controller 64 transmits the condition, parameter, time and location information wirelessly directly or indirectly through a base station to a central control via the transceiver 70 and the antenna 72 and/or the antenna 73. The controller 64 can transmit the information periodically, in response to a poll or request from the central control or when a change of conditions or event has occurred. The controller 64 can be operative to receive reset requests, status requests, and receive software updates from the central control via the transceiver 70 and the antenna 72 and/or antenna 73.

It is to be appreciated that the SA beacon portion 60 can be a stand-alone unit that can add wireless functionality to a variety of different data collection devices via a connection port (e.g., a serial interface, parallel interface). It is also to be appreciated that the SA beacon portion 60 can be employed as a stand-alone wireless repeater in a system such as that illustrated in FIG. 1, for example, employing the first antenna 72 to receive communications and the second antenna 73 to transmit communications. It is further appreciated that the SA beacon portion 60 can provide the capability to interpret data in various forms and present the data in various forms.

Figure 3:
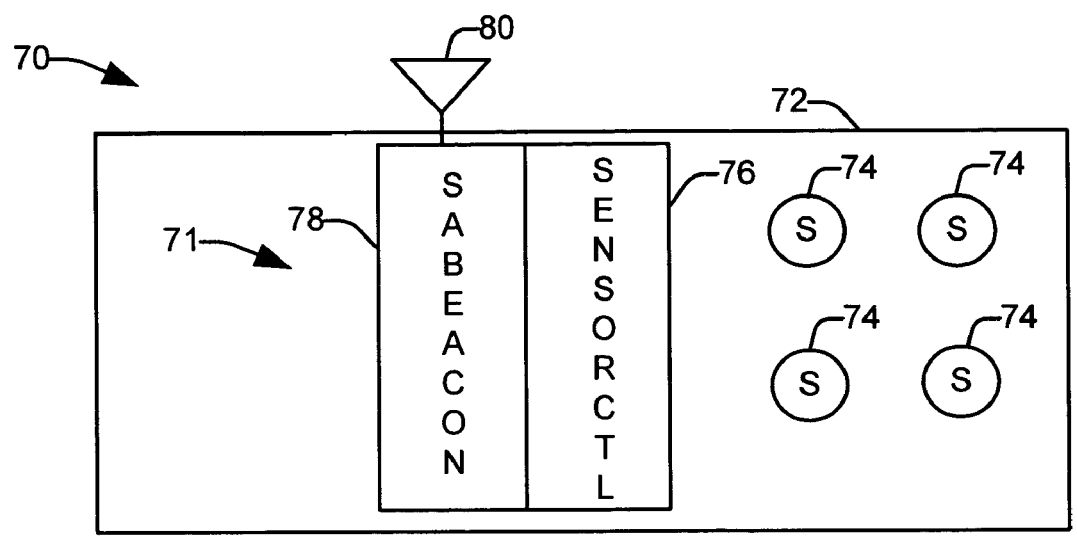
FIG. 3 illustrates a condition and location monitoring system employed in a heart monitor in accordance with an aspect of the present invention.

FIG. 3 illustrates a condition and location monitoring system employed in a heart monitor system 70 in accordance with an aspect of the present invention. The heart monitor system 70 includes a condition and location system coupled to a belt strap 72 that can be wrapped around a chest of a heart patient. The belt strap 72 includes a plurality of integrated sensors 74 disposed at a location that can be positioned overlying a heart of a heart patient. The condition and location monitoring system 71 includes a sensor control portion 76 coupled to the plurality of integrated sensors 74, and a SA beacon portion 78 coupled to the sensor control portion 76. The plurality of integrated sensors 74 can monitor real time parameters such as heart rate, heart rhythm, blood pressure, body temperature, perspiration and other real time parameters. The sensor control 76 compares the monitored parameters to one or more predetermined thresholds to determine a heart condition of a patient. The condition information is provided to the SA beacon portion 78. The SA beacon portion 78 includes a GPS device for determining location of the heart patient. The SA beacon portion 78 is operative to transmit the heart patient's condition information and location information back to a central control. In this manner, if an alert condition occurs, the location and condition of the patient can be transmitted back to the central control for display, for example, at a hospital. The hospital personnel can then react and locate the patient for immediate attention if needed.

Figure 4:
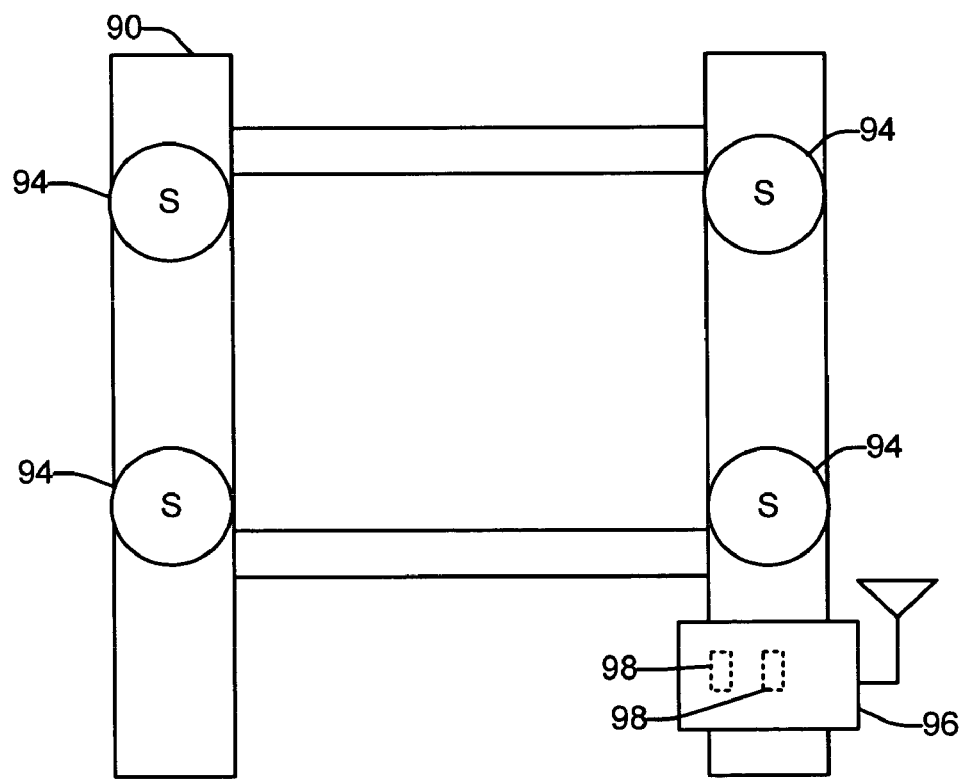
FIG. 4 illustrates a condition and location monitoring system employed in Multiple Integrated Laser Engagement System (MILES) training vest in accordance with an aspect of the present invention.

FIG. 4 illustrates a condition and location monitoring system 96 employed in Multiple Integrated Laser Engagement System (MILES) training vest 90 in accordance with an aspect of the present invention. The training vest 90 includes a plurality of detectors or sensors 94 that detect or sense laser fire in the form of a laser transmission to the detector from a MILES weapon. The detectors or sensors 94 are electrically coupled to a sensor control portion of the condition monitoring and location system 96 located on the vest 90. The plurality of sensors 94 and the sensor control are provided as part of a standard MILES training vest. The sensor control is a stand-alone unit of the MILES training vest and includes input control and an infrared communication ports 98 for retrieving condition (e.g., live, dead, injured) and parameter information (e.g., current player Identification, type of weapon which current player was hit, player identification of which player hit the current player, location of hit, time of hit). The condition information can be determined by comparing the parameter information, such as whether a hit has occurred or the type of weapon to one or more thresholds, such as whether the type of weapon causes injury or death. The infrared communication ports 98 can be also used to receive reset commands, status requests and software updates.

Figure 5:
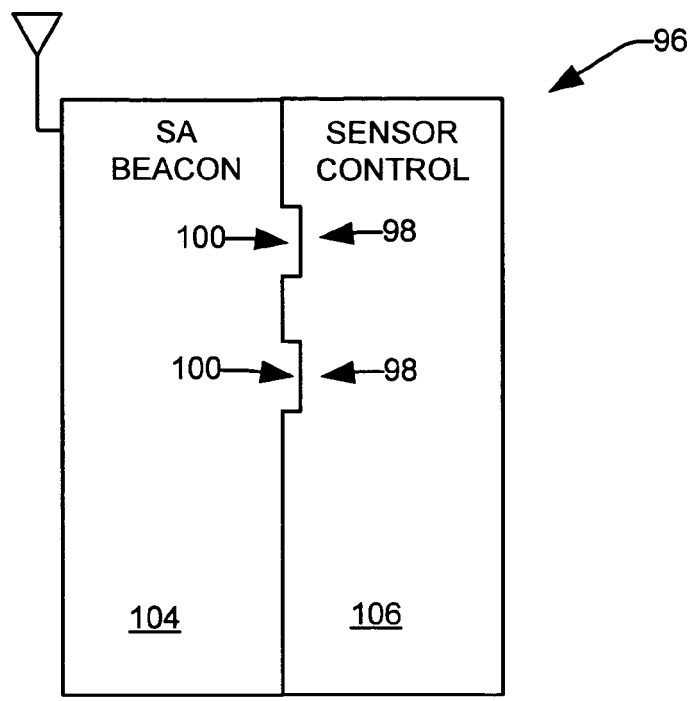
FIG. 5 illustrates a side view of the condition and location monitoring system of FIG. 4.

The sensor control is coupled to a SA beacon portion. The SA beacon portion is separate unit from the MILES sensor control portion. FIG. 5 illustrates a side view of the condition and location monitoring system 96 of FIG. 4. As illustrated in FIG. 5, the condition and location monitoring system 96 includes a sensor control portion 106 integral to the MILES vest 90. A separate SA beacon portion 104 is coupled to the sensor control portion 106 via a fastening mechanism (e.g., screws, fasteners, releasable engageable strap) (not shown). The SA beacon portion 104 is communicatively coupled via an infrared interface 100 to infrared ports 98 of the sensor control 106. Referring to both FIGS. 4-5, the SA beacon 104 includes a GPS device for determining a location of the player wearing the MILES vest 90. The SA beacon 104 also retrieves the condition information and parameter information from the sensor control 106. The location information, condition information and parameter information are transmitted back to a central control periodically or in response to a status request via a transceiver and an antenna. The SA beacon 104 can also receive commands from the central control to reset the sensor control 106, update software of the SA beacon 104 or sensor control 106 or retrieve condition and parameter information from the sensor control 106.

Figure 6:
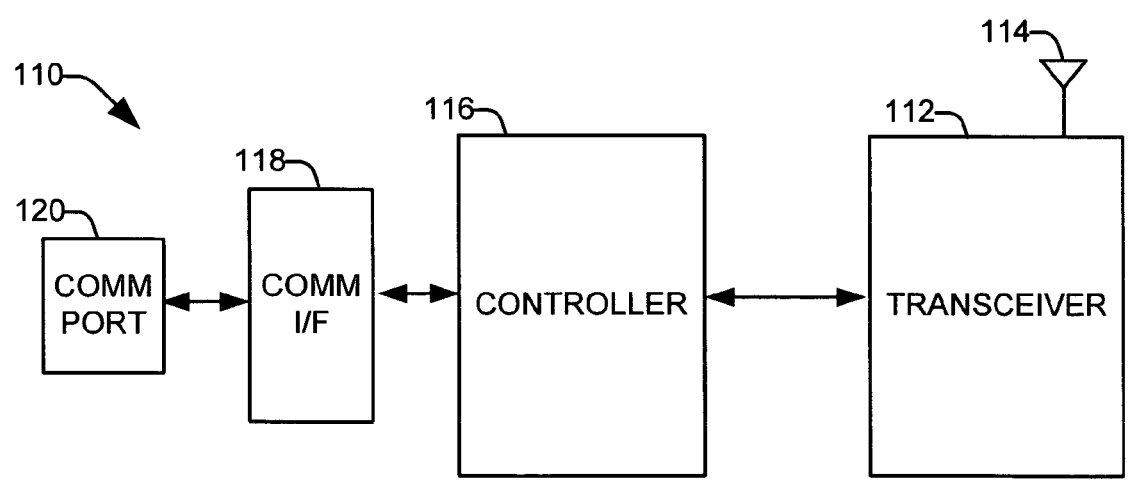
FIG. 6 illustrates a block diagram of an exemplary base station in accordance with an aspect of the present invention.

FIG. 6 illustrates a block diagram of an exemplary base station 110. The base station 110 includes a transceiver 112 and an antenna 114 for wirelessly communicating with a condition and location monitoring system. The base station 110 includes a controller 116 that is operative to translate communications between radio frequency formats and computer displayable formats, such as a text markup language (e.g., dynamic markup language (XML), hypertext markup language (HTML)). The base station 110 also includes a communication interface 118, such as an Ethernet card and a communication port 120, such as an Ethernet port. It is to be appreciated that a variety of other communication formats, interfaces and ports can be employed to convert radio communications to computer displayable formats. The controller 116 can also include functionality of translating radio communications from a variety of communication formats and modulations to a variety of different computer displayable formats. As previously discussed, the base station 110 can be employed to route communications between a plurality of condition and location monitoring systems and a central control.

Figure 7:
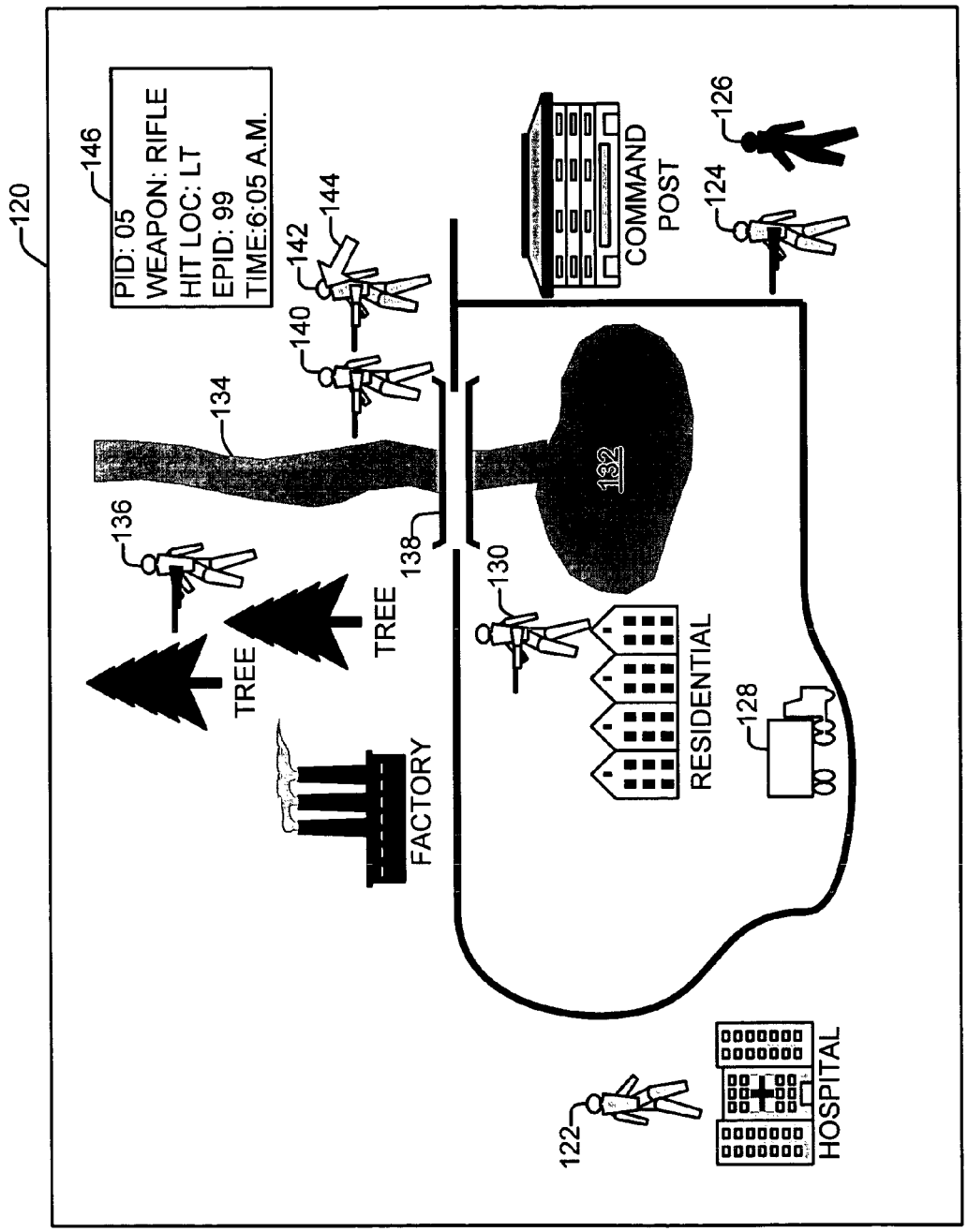
FIG. 7 illustrates an exemplary display of a central control in accordance with an aspect of the present invention.

FIG. 7 illustrates an exemplary display 120 at a central control in accordance with an aspect of the present invention. The exemplary display 120 is illustrated with respect to a MILES training exercise. It is to be appreciated that a MILES training exercise is just one exemplary implementation, and a variety of other implementations can be contemplated employing the situational awareness system of the present invention. In the exemplary display, a white player icon indicates that a player is alive, a grey player icon indicated that a player is injured, while a black player icon indicated that a player is dead. A black rifle indicates a rifle that is out of ammunition, while a white rifle indicates a rifle that still has ammunition. The condition of the player and the player's weapon are indicated based on color of the player and weapon. The target for the training exercise is an enemy factory. The enemy players are not displayed on the exemplary display. However, the enemy players could be displayed on the exemplary display in accordance with an aspect of the present invention.

Each of the players is wearing a MILES vest with a sensor control coupled to a SA beacon in accordance with an aspect of the invention. The sensor control determines the condition of the player and the player's weapon. Alternatively, a separate sensor control can be provided for the player's weapon. A SA beacon is coupled to the sensor control to transmit condition and location information back to a central control for display. The central control and associated display can reside at a command center and/or hospital. The central control displays the location and conditions associated with a plurality of friendly players in a geographic map illustrating the training exercise field. The central control can periodically poll each player for condition and location information status in addition to parameter information.

As illustrated in the display 120, an injured player 122 resides at the hospital. A killed player 126 and another injured player 124 having a rifle without ammunition is located near the command post. A truck 128 has been deployed from the hospital to retrieve the killed player 126 and the injured player 124. A live player 130 with ammunition resides near a residential complex by a lake 132. A live player 136 without ammunition resides in a forest, indicated by trees, by a river 134. A live player 140 with ammunition and an injured player 142 with ammunition are located near a bridge 138 overlying the river 134. A mouse pointer 144 is pointed to the injured player 142, which causes a display 146 of parameter information to be provided. As illustrated in the example, the injured player 142 is player ID 005 was hit by a rifle shot in the lower torso (LT), by enemy player ID (PID) 99 at 6:05 A.M. The longitude and latitude of the player can also be displayed. The exemplary display 120 provides real time condition, location and parameter information for a plurality of players.

Figure 8:
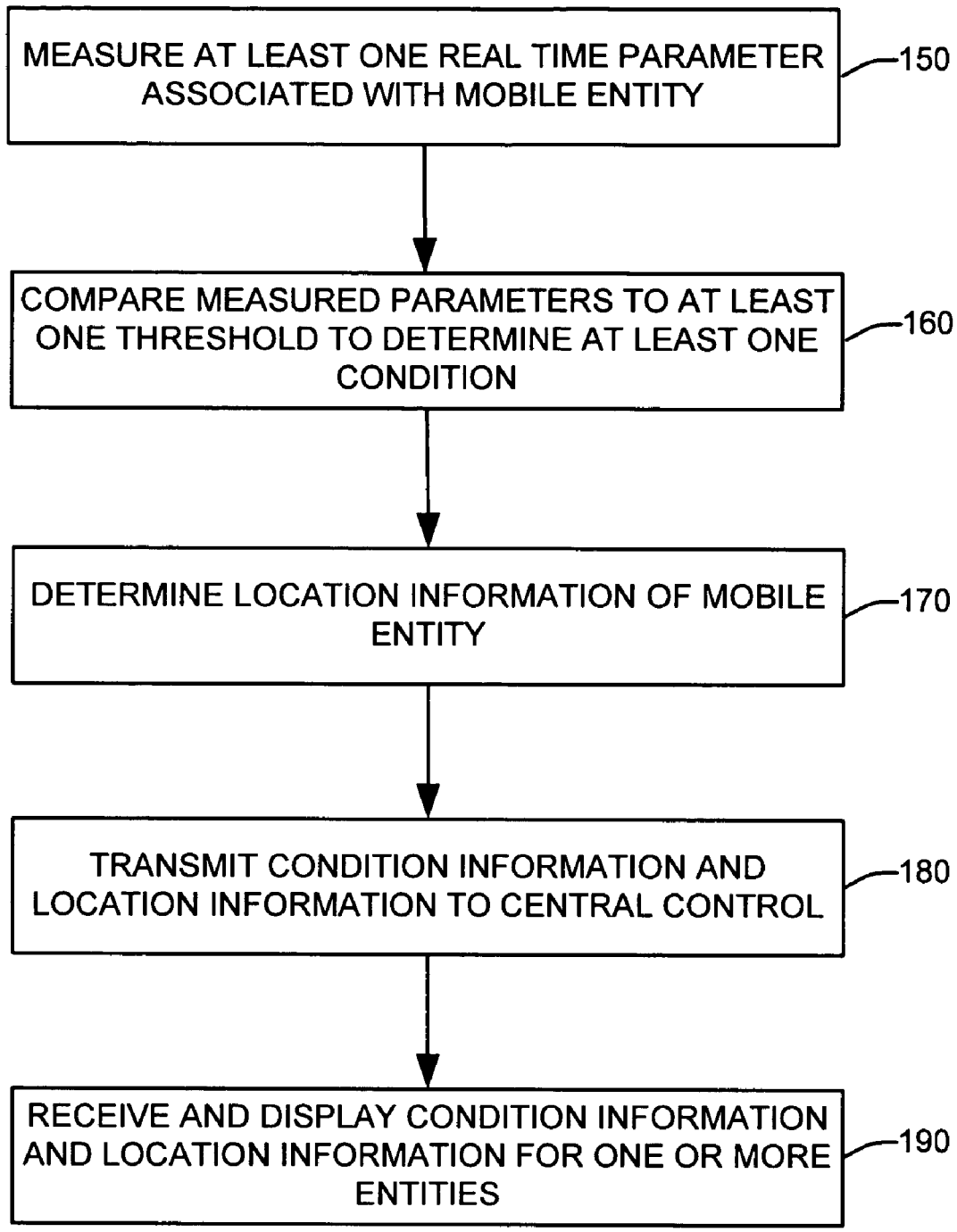
FIG. 8 illustrates an exemplary methodology for condition and location monitoring in accordance with an aspect of the present invention.

In view of the foregoing structural and functional features described above, a method will be better appreciated with reference to FIG. 8. It is to be understood and appreciated that the illustrated actions, in other embodiments, may occur in different orders and/or concurrently with other actions. Moreover, not all illustrated features may be required to implement a method. It is to be further understood that the following methodologies can be implemented in hardware (e.g., a computer or a computer network as one or more integrated circuits or circuit boards containing one or more microprocessors), software (e.g., as executable instructions running on one or more processors of a computer system), or any combination thereof.

FIG. 8 illustrates a methodology for condition and location monitoring in accordance with an aspect of the present invention. The methodology begins at 150 where one or more real time parameters associated with a mobile entity are measured. The one or more real time parameters can be parameters associated with a living mobile entity, a non-living mobile entity or an environment of the mobile entity. At 160, the measured one or more real time parameters are compared to one or more predetermined thresholds to determine one or more conditions associated with the mobile entity. A condition can be determined by determining if a parameter value falls within a threshold range, for example, for a predetermined time period. At 170, location information associated with the mobile entity is determined. The location information can be determined by employing a GPS device. At 180, condition information and location information is transmitted to a central control. The condition information and location information can be transmitted periodically or in response to a status poll from the central control. At 190, the condition information and location information is displayed for one or more mobile entities. The condition information and location information can be displayed by displaying icons in a geographic map representing the mobile entities, with different colors representing different conditions. Alternatively, the information can be displayed textually. Additionally, the parameter information can be transmitted and displayed in conjunction with the condition and location information.

Figure 9:
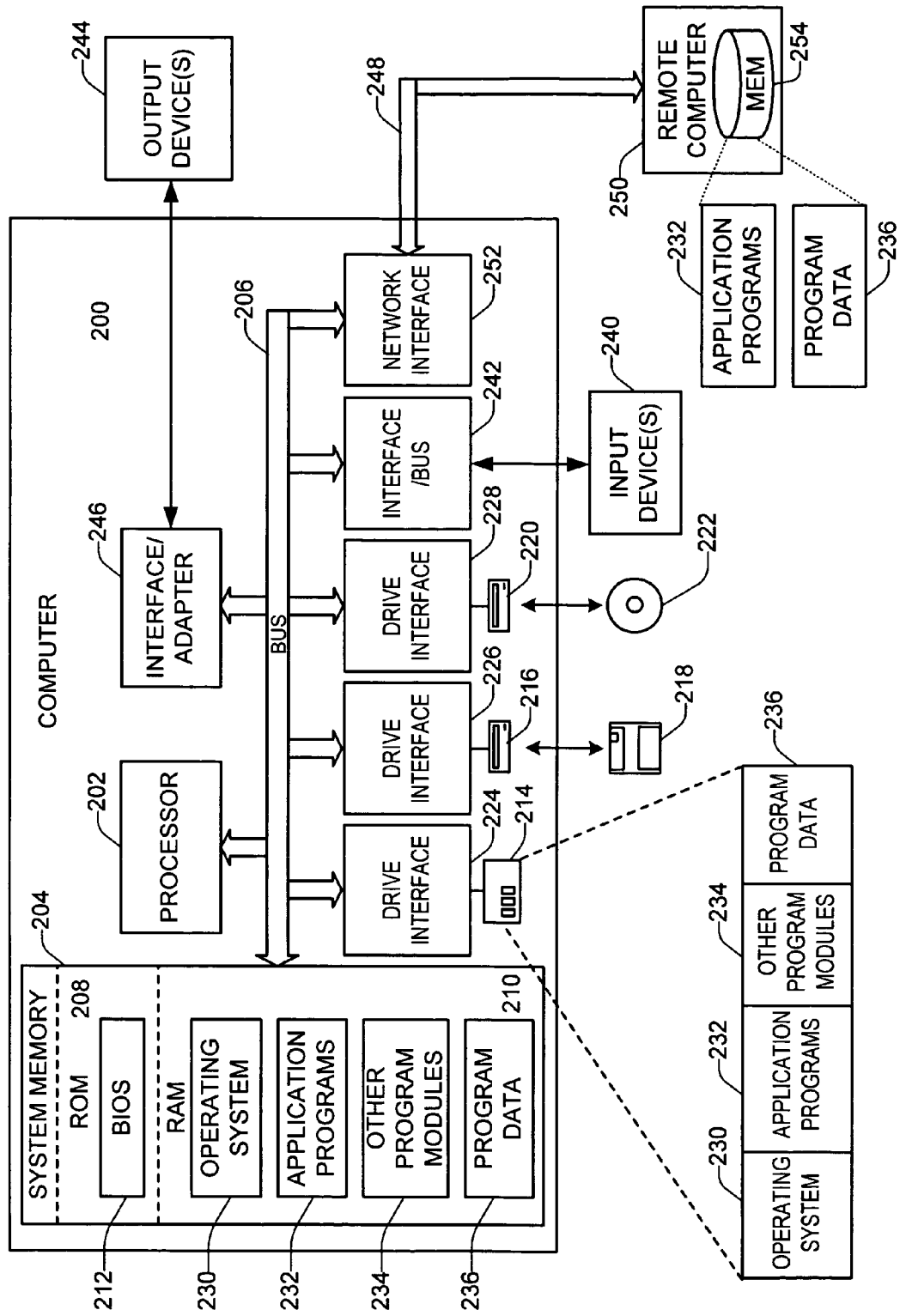
FIG. 9 illustrates an embodiment of a computer system for employment of a central control in accordance with an aspect of the present invention.

FIG. 9 illustrates a computer system 200 that can be employed to implement the central control and display described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. A system bus 206 couples various system components, including the system memory 204 to the processor 202. Dual microprocessors and other multi-processor architectures can also be utilized as the processor 202. The system bus 206 can be implemented as any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) 212 can reside in the ROM 208, generally containing the basic routines that help to transfer information between elements within the computer system 200, such as a reset or power-up.

The computer system 200 can include a hard disk drive 214, a magnetic disk drive 216, e.g., to read from or write to a removable disk 218, and an optical disk drive 220, e.g., for reading a CD-ROM or DVD disk 222 or to read from or write to other optical media. The hard disk drive 214, magnetic disk drive 216, and optical disk drive 220 are connected to the system bus 206 by a hard disk drive interface 224, a magnetic disk drive interface 226, and an optical drive interface 228, respectively. The drives and their associated computer-readable media provide nonvolatile storage of data, data structures, and computer-executable instructions for the computer system 200. Although the description of computer-readable media above refers to a hard disk, a removable magnetic disk and a CD, other types of media which are readable by a computer, may also be used. For example, computer executable instructions for implementing systems and methods described herein may also be stored in magnetic cassettes, flash memory cards, digital video disks and the like.

A number of program modules may also be stored in one or more of the drives as well as in the RAM 210, including an operating system 230, one or more application programs 232, other program modules 234, and program data 236.

A user may enter commands and information into the computer system 200 through user input device 240, such as a keyboard, a pointing device (e.g., a mouse). Other input devices may include a microphone, a joystick, a game pad, a scanner, a touch screen, or the like. These and other input devices are often connected to the processor 202 through a corresponding interface or bus 242 that is coupled to the system bus 206. Such input devices can alternatively be connected to the system bus 206 by other interfaces, such as a parallel port, a serial port or a universal serial bus (USB). One or more output device(s) 244, such as a visual display device or printer, can also be connected to the system bus 206 via an interface or adapter 246.

The computer system 200 may operate in a networked environment using logical connections 248 to one or more remote computers 250. The remote computer 250 may be a workstation, a computer system, a router, a peer device or other common network node, and typically includes many or all of the elements described relative to the computer system 200. The logical connections 248 can include a local area network (LAN) and a wide area network (WAN).

When used in a LAN networking environment, the computer system 200 can be connected to a local network through a network interface 252. When used in a WAN networking environment, the computer system 200 can include a modem (not shown), or can be connected to a communications server via a LAN. In a networked environment, application programs 232 and program data 236 depicted relative to the computer system 200, or portions thereof, may be stored in memory 254 of the remote computer 250.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for condition and location monitoring of mobile entities in a Multiple Integrated Laser Engagement System (MILES) training exercise, the system comprising:
    a situational awareness (SA) beacon associated with each of a given MILES training sensor system, the SA beacon comprising:
        a global position satellite (GPS) device that determines a location of the MILES training sensor system;
        a communication interface configured to provide communications with the MILES training sensor system through an infrared communication port of the MILES training sensor system;
        a controller configured to transmit commands to and receive condition information from a sensor control of the MILES training sensor system through the communication interface and the infrared communication port;
        a fastening mechanism that couples the SA beacon to the MILES training sensor system and communicatively couples the communication interface to the infrared communication port; and
        a transceiver that transmits location information and condition information associated with the MILES training sensor system to a remote device.

2. The system of claim 1, further comprising a central control that receives condition information and location information from a plurality of SA beacons associated with respective ones of the plurality of MILES training sensor systems in a geographic map.

3. The system of claim 2, wherein the SA beacon transmits location information and condition information to the central control in response to a status request from the central control.

4. The system of claim 1, wherein the SA beacon transmits location information and condition information to a central control upon a change of condition of a MILES training sensor system indicting that an event has occurred with respect to the MILES training sensor system.

5. The system of claim 1, wherein at least one of the MILES training sensor systems is a MILES training vest configured to be worn by a player in the MILES training exercise.

6. The system of claim 5, wherein the condition information is whether a mobile entity is live, dead or injured due to laser fire from a weapon received or not received by the MILES training vest.

7. The system of claim 6, wherein the SA beacon also transmits parameter information with the location information and the condition information, the parameter information being at least one of current player identification, a type of weapon which a current player was hit, a player identification of which player hit a current player, a location information of a hit, and a time of a hit.

8. The system of claim 6, wherein the controller is operative to receive status requests, reset commands and software updates for at least one of the SA beacon and the MILES training sensor systems from a central control.

9. The system of claim 1, further comprising a base station that routes communication between SA beacons and the central control, wherein the base station translates radio communications from the SA beacons to a text markup language for display at a central control.

10. The system of claim 1, wherein the condition information associated with each of the plurality of MILES training sensor systems is displayed in a geographic map at a central control by varying an icon color associated with an icon representing a respective mobile entity employing a respective MILES training sensor system, and the location information associated with each of the plurality of mobile entities is displayed by locating the icon in a location of the geographic map associated with an area in which the respective MILES training sensor system is moving.

11. A situational awareness system comprising:
    a plurality of condition and location monitoring systems that determine at least one condition and a location of an associated mobile entity, wherein the at least one condition is based on a measured real time parameter value associated with an associated mobile entity being compared to at least one predetermined threshold; and
    a central control that receives the condition information and location information from the plurality of condition and location monitoring systems and displays icons representing the plurality of mobile entities in a geographic map representing an area in which the plurality of mobile entities move, wherein the condition information associated with each of the plurality of mobile entities is displayed in a geographic map by varying an icon color associated with an icon representing a respective mobile entity, and the location information associated with each of the plurality of mobile entities is displayed by locating the icon in a location of the geographic map.

12. The system of claim 11, wherein the condition is based on a measured real time parameter value being within a threshold range for a predetermined amount of time.

13. The system of claim 11, wherein each of the plurality of condition and location monitoring systems comprise:
    a sensing system having at least one sensor and a sensor control that determines the at least one condition by comparing the measured real time parameter value provided by the at least one sensor to the at least one predetermined threshold; and a situational awareness (SA) beacon comprising a global position satellite (GPS) device that determines a location of the mobile entity and a transceiver, wherein the SA beacon periodically transmits location information and condition information via the transceiver to the central control for display.

14. The system of claim 11, wherein a given condition and location monitoring systems transmits location information and condition information to a central control in response to a change in condition of the respective mobile entity.

15. The system of claim 11, wherein the central control is operative to transmit status poll requests, reset commands and software updates to each of the condition and location monitoring systems.

16. A condition and location monitoring system for mobile entities in a Multiple Integrated Laser Engagement System (MILES) training exercise, the system comprising:
  a situational awareness (SA) beacon associated with each of a given MILES training sensor system, the SA beacon comprising:
    means for measuring at least one real time parameter associated with the MILES training sensor system;
    means for determining a condition of the mobile entity based on a comparison of the at least one real time parameter to at least one predetermined threshold;
    means for determining a location of the mobile entity;
    means for sending and receiving infrared communications of commands and condition information with the MILES training sensor system;
    means for fastening the SA beacon to the MILES training sensor system such that the SA beacon and the MILES training sensor system are in infrared communication; and
    means for periodically transmitting condition and location information of the mobile entity to a central control.

17. The system of claim 16, further comprising means for converting the condition and location information into a displayable format, and means for displaying the condition and location information in a geographic map in which the MILES training sensor system is moving.

18. The system of claim 16, wherein the condition information is whether a mobile entity is live, dead or injured due to laser fire from a weapon received or not received by the MILES training sensor system.

19. The system of claim 16, wherein the means for periodically transmitting condition and location information of the MILES training sensor system transmits condition and location information in response to one of a status request from the central control and a change in condition indicating an event has occurred.

20. A method for condition and location monitoring of a mobile entities in a Multiple Integrated Laser Engagement System (MILES) training exercise, the method comprising:
  fastening a situational awareness (SA) beacon to a given MILES training sensor system such that the SA beacon and the MILES training sensor system are in infrared communication;
  comparing at least one measured real time parameter associated with a a MILES training sensor system to at least one predetermined threshold to determine at least one condition associated with the mobile entity;
  determining a location of the mobile entity; and
  transmitting condition information and location information associated with the MILES training sensor system to a central control.

21. The method of claim 20, further comprising performing the comparing, determining and transmitting for a plurality of MILES training sensor systems for display at the central control.

22. The method of claim 21, further comprising displaying the condition information and location information for the plurality MILES training sensor systems, performing the comparing, determining and transmitting for the plurality of MILES training sensor systems for display at the central control, wherein the condition information associated with each of the MILES training sensor systems is displayed in a geographic map by varying an icon color associated with an icon representing a respective mobile entity, and the location information associated with each of the plurality MILES training sensor systems is displayed by locating the icon in a location of the geographic map.

23. The method of claim 20, wherein transmitting condition and location information of the MILES training sensor system is performed in response to one of a status request from the central control and a change in condition of a respective mobile entity indicating an event has occurred with respect to the respective MILES training sensor system.

* * * * *